US008647387B2

(12) United States Patent
Winslow

(10) Patent No.: US 8,647,387 B2
(45) Date of Patent: Feb. 11, 2014

(54) METHOD AND APPARATUS FOR TRIALING A MODULAR HUMERAL HEAD

(75) Inventor: Nathan A. Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 173 days.

(21) Appl. No.: 13/204,194

(22) Filed: Aug. 5, 2011

(65) Prior Publication Data
US 2011/0295376 A1 Dec. 1, 2011

Related U.S. Application Data

(63) Continuation of application No. 11/076,293, filed on Mar. 9, 2005, now Pat. No. 8,052,758.

(51) Int. Cl.
A61F 2/40 (2006.01)
(52) U.S. Cl.
USPC ........................................ 623/19.14; 128/898
(58) Field of Classification Search
USPC ........................................ 623/22.11–22.36
See application file for complete search history.

(56) References Cited

U.S. PATENT DOCUMENTS

| 3,815,157 A | 6/1974 | Skorecki et al. |
| 3,869,730 A | 3/1975 | Skobel |
| 3,978,528 A | 9/1976 | Crep |
| 4,003,095 A | 1/1977 | Gristina |
| 4,040,131 A | 8/1977 | Gristina |
| 4,042,980 A | 8/1977 | Swanson et al. |
| 4,135,517 A | 1/1979 | Reale |
| 4,822,370 A | 4/1989 | Schelhas |
| 4,865,605 A | 9/1989 | Dines et al. |
| 4,865,609 A | 9/1989 | Roche |
| 4,919,670 A | 4/1990 | Dale et al. |
| 4,957,510 A | 9/1990 | Cremascoli |
| 4,963,155 A | 10/1990 | Lazzeri et al. |
| 5,080,685 A | 1/1992 | Bolesky et al. |
| 5,135,529 A | 8/1992 | Paxson et al. |
| 5,181,928 A | 1/1993 | Bolesky et al. |
| 5,201,882 A | 4/1993 | Paxson |
| 5,222,984 A | 6/1993 | Forte |
| 5,314,479 A | 5/1994 | Rockwood, Jr. et al. |
| 5,358,526 A | 10/1994 | Tornier |

(Continued)

FOREIGN PATENT DOCUMENTS

| DE | 19509037 C1 | 9/1996 |
| EP | 0257359 A1 | 3/1988 |

(Continued)

OTHER PUBLICATIONS

"Buechel-Pappas Total Shoulder System," Endotec, Jul. 1991.

(Continued)

Primary Examiner — David Isabella
Assistant Examiner — Ann Schillinger
(74) Attorney, Agent, or Firm — Harness, Dickey

(57) ABSTRACT

The present disclosure is directed to a modular shoulder prosthesis measuring device having an adjustable radial offset provided by relative rotation of an adapter interdisposed between the stem and the head. Specifically, the interface configuration between the stem and the adapter, as well as between the adapter and the head are designed such that relative positioning of these components provides a continuous adjustment in the radial offset. Indicia are provided to precisely determine the magnitude and direction of the adjustment being made.

11 Claims, 6 Drawing Sheets

(56) References Cited

U.S. PATENT DOCUMENTS

| | | | |
|---|---|---|---|
| 5,507,817 A | 4/1996 | Craig et al. | |
| 5,507,824 A | 4/1996 | Lennox | |
| 5,549,682 A | 8/1996 | Roy | |
| 5,580,352 A | 12/1996 | Sekel | |
| 5,658,340 A | 8/1997 | Muller et al. | |
| 5,702,457 A | 12/1997 | Walch et al. | |
| 5,702,486 A | 12/1997 | Craig et al. | |
| 5,728,161 A | 3/1998 | Camino et al. | |
| 5,902,340 A | 5/1999 | White et al. | |
| 5,910,171 A | 6/1999 | Kummer et al. | |
| 5,961,555 A | 10/1999 | Huebner | |
| 6,015,437 A | 1/2000 | Stossel | |
| 6,033,439 A | 3/2000 | Camino et al. | |
| 6,102,953 A * | 8/2000 | Huebner | 623/19.11 |
| 6,129,764 A | 10/2000 | Servidio | |
| 6,171,341 B1 | 1/2001 | Boileau et al. | |
| 6,197,062 B1 | 3/2001 | Fenlin | |
| 6,197,063 B1 | 3/2001 | Dews | |
| 6,206,925 B1 | 3/2001 | Tornier | |
| 6,228,120 B1 | 5/2001 | Leonard et al. | |
| 6,368,352 B1 | 4/2002 | Camino et al. | |
| 6,736,852 B2 | 5/2004 | Callaway et al. | |
| 6,749,637 B1 | 6/2004 | Bahler | |
| 6,942,699 B2 | 9/2005 | Stone et al. | |
| 2001/0049561 A1* | 12/2001 | Dews et al. | 623/19.14 |
| 2002/0016634 A1 | 2/2002 | Maroney et al. | |
| 2003/0028253 A1* | 2/2003 | Stone et al. | 623/19.14 |
| 2003/0149485 A1 | 8/2003 | Tornier | |
| 2004/0030394 A1 | 2/2004 | Horber | |
| 2004/0064188 A1 | 4/2004 | Ball et al. | |

FOREIGN PATENT DOCUMENTS

| | | |
|---|---|---|
| EP | 0599429 A2 | 6/1994 |
| EP | 0664108 A2 | 7/1995 |
| EP | 0679375 A1 | 11/1995 |
| EP | 0712617 A1 | 5/1996 |
| EP | 0797964 A1 | 10/1997 |
| FR | 2574283 A1 | 6/1986 |
| FR | 2652498 A1 | 4/1991 |
| FR | 2664809 A1 | 1/1992 |
| FR | 2721200 A1 | 12/1995 |
| WO | 9522302 A1 | 8/1995 |
| WO | 9617553 A1 | 6/1996 |
| WO | 9846172 A1 | 10/1998 |
| WO | 0015154 A1 | 3/2000 |

OTHER PUBLICATIONS

Final Office Action for U.S. Appl. No. 11/076,293 Mailed Jan. 21, 2009.
Final Office Action for U.S. Appl. No. 11/076,293 Mailed Mar. 29, 2011.
Final Office Action for U.S. Appl. No. 11/076,293 Mailed Nov. 16, 2007.
Non-Final Office Action for U.S. Appl. No. 11/076,293 Mailed Apr. 20, 2007.
Non-Final Office Action for U.S. Appl. No. 11/076,293 Mailed Jun. 25, 2008.
Non-Final Office Action for U.S. Appl. No. 11/076,293 Mailed Sep. 13, 2010.
Thabe et al., "Die endoprothetische Versorgung des rheumatischen Schultergelenkes," Aktuelle Rheumatologie, vol. 19 (1994), pp. 155-160 (with English Abstract).
Thabe et al., "Modulares—Vario—Schulter," 6 sheets of pictures, Oct. 2004.

* cited by examiner

METHOD AND APPARATUS FOR TRIALING A MODULAR HUMERAL HEAD

CROSS-REFERENCE TO RELATED APPLICATIONS

This application is a continuation of U.S. patent application Ser. No. 11/076,293 filed on Mar. 9, 2005. The disclosure of the above application is incorporated herein by reference.

FIELD

The present disclosure relates to a prosthesis for replacing and reconstructing a portion of the humerus and more specifically to a trialing system for a modular humeral prosthesis which allows for shoulder joint replacement.

BACKGROUND

The present disclosure relates to a prosthesis for replacing and reconstructing a portion of the humerus and more specifically to a modular humeral prosthesis which allows for shoulder joint replacement.

The shoulder joint is considered to be one of the most complex joints in the body. The scapula, the clavicle and the humerus all meet at the shoulder joint. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthropathy, avascular necrosis, bone fracture or failure of previous joint implants. If severe joint damage occurs and no other means of treatment is found to be effective, then shoulder reconstruction may be necessary.

A shoulder joint prosthesis generally includes the replacement of the ball of the humerus and, optionally, the socket of the shoulder blade with specially designed artificial components. The bio-kinematics, and thus the range of motion in the shoulder vary greatly among prospective patients for reconstruction shoulder surgery. The humeral component typically has a metal shaft or stem with a body portion that is embedded in the resected humerus and a generally hemispherical head portion supported on the stem. The head slidingly engages a glenoid implant on the glenoid fossa. During reconstructive surgery, the components of the prosthesis are matched with the bio-kinematics of the patient in an effort to maintain the natural range of motion of a healthy shoulder joint. Thus, a shoulder prosthesis design must be readily adaptable to a wide range of bio-kinematics for prospective patients.

In this regard, shoulder prostheses are generally available as either unitary structures or modular components. With unitary shoulder prosthesis, a large inventory of differently sized prostheses must be maintained to accommodate the different bone sizes and joint configurations of the prospective patients. With such unitary shoulder prosthesis, the patient is typically evaluated by x-ray to determine the approximate prostheses size needed for reconstruction. A number of differently sized prostheses are selected as possible candidates based upon this preliminary evaluation. Final selection of the appropriately sized prosthesis is made during the surgery. With unitary shoulder prosthesis, each design may represent a compromise that is unable to achieve all of the natural range of motion of a healthy shoulder joint because of the fixed geometric configuration in their design.

Modular prostheses systems which reduce the need to maintain large inventories of various sized components are well known in the art. Conventionally, the humeral prosthesis includes two components—a humeral stem component and a spherical head releasably coupled to the stem. Alternately, a three component design is known in which the stem and shoulder are interconnected with an adapter. In either of the two-piece or three-piece designs, a radial offset or angulator inclination of the head relative to the stem is provided in individual components. Different radial offsets or angular inclinations are achieved through the use of different adapters or heads. In this regard, conventional modular shoulder prosthesis kits include multiple redundant components such as adapters and heads to achieve a range of prosthetic options.

While providing an advantage over the unitary design in reducing the number of components needed, a rather large inventory of head components and/or adapter components must be maintained to provide the desired range of geometric configurations with the conventional modular shoulder prostheses. These components are readily adaptable to provide a range of geometric configurations, i.e. radial offsets of angular inclination while minimizing the number of components required. There is, therefore, a need for a trialing system and method for determining which of these components are needed and their specific orientation.

SUMMARY

In accordance with the teachings of the present disclosure a modular joint prosthesis system is provided. Specifically, a humeral component for a shoulder prosthesis includes an adapter and a head component which cooperate to provide a range of radial offsets and/or angular inclinations and which are adapted to be used in conjunction with a stem.

According to one exemplary embodiment, a measuring instrument for humeral component for a shoulder prosthesis is provided for determining the needed adjustable radial offset of the head with respect to the stem. The present disclosure includes an adapter interposed between a stem and a head. The adapter is slidably coupled to the head such that relative linear positioning of the adapter on the head will effect a first adjustment in the radial offset. Likewise, the adapter component is rotationally coupled to the stem as such that relative angular position of the adapter will effect a rotational offset adjustment. By selectively positioning the adapter with respect to the head, an infinite adjustment of the radial offset within a given range may be achieved. Indicia are provided at the interface between the adapter and the head to indicate the offset vector (i.e., offset amount and direction).

According to another exemplary embodiment, a measuring instrument for a humeral component for a shoulder prosthesis is provided for determining the adjustable radial offset of the head with respect to the stem. The present disclosure includes an adapter interposed between a stem and a head. The adapter is slidably coupled to a cavity formed in the head such that relative linear positioning of the adapter on the head will effect a first adjustment in the radial offset of the head. Likewise, the adapter component is rotationally coupled to the stem as such that relative angular position of the stem on the adapter will effect a rotational offset adjustment. A fastener is provided to fix the location of the head to the adapter. In one example, indicia are provided on the adapter and the head to indicate the offset vector.

The joint prosthesis measurement system of the present disclosure provides great flexibility in the adjustment of important bio-kinematic parameters for the prosthesis systems while allowing for the minimizing the number of components required for the modular system. These and other features of the present disclosure will become apparent from the description and especially taken in conjunction with the accompanying drawings. It should be understood that the detailed description and specific examples are intended for purposes of illustration only and are not intended to limit the scope of the present disclosure.

BRIEF DESCRIPTION OF THE DRAWINGS

The present disclosure will become more fully understood from the detailed description and the accompanying drawings, wherein.

DETAILED DESCRIPTION

The following description is merely exemplary in nature and is in no way intended to limit the present disclosure, its application, or uses.

Figure 1:
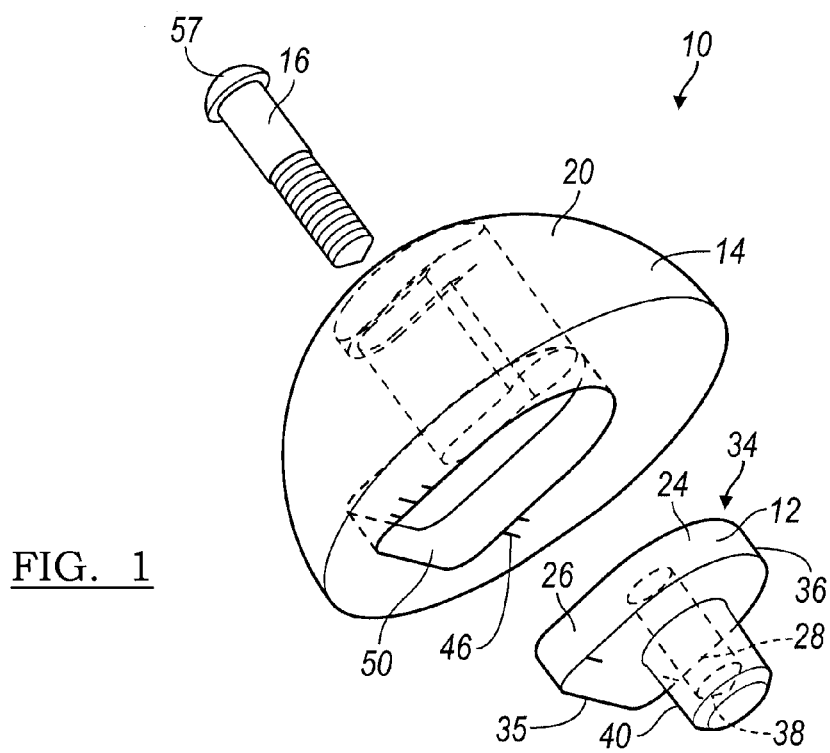
FIG. 1 is an exploded front view of a modular shoulder prosthesis measurement system in accordance with the present teachings.

FIG. 1 is an exploded front view of a modular shoulder prosthesis measurement system according to the present teachings. The measuring device 10 is formed of an adapter 12, a head 14, and a coupling member 16. The adapter 12 is preferably formed of a polymer material, which allow its relative rotation with respect to a fixation member or stem 18. The measuring device 10 is configured to determine both the needed radial offset of an implant head with respect to an implanted fixation member, and also the rotational offset of the head with respect to the fixation member. As further described below, the adapter 12 is slidably coupled to the head 14 such that relative linear positioning of the adapter 12 with the head 14 will affect a first adjustment in the radial offset. Selected positioning of the adapter 12 with respect to the head 14 gives an infinite adjustment of the radial offset within a given range.

Referring generally to FIG. 1, FIGS. 4A-4C and FIG. 6, the adapter 12 has a body portion 24, having a first pair of bearing surfaces 26 and 28. The first pair of bearing surfaces 26 and 28 are slidably coupled to a second pair of bearing surfaces 30 and 32 defined on the head 14. The body portion 24 further has a flat stop surface 35 and a circular stop surface 36 which function to limit the movement of the adapter 12 with respect to the head 14. The adapter 12 further defines a coupling member accepting bore 38 which is optionally threaded. A tapered coupling portion 40 is configured to interface with a Morse taper coupling feature on the stem 18. This tapered coupling portion 40, while shown as a male taper, may optionally be a female taper configured to interface with a male Morse taper formed on the stem 18 or any other connection member.

Figure 2:
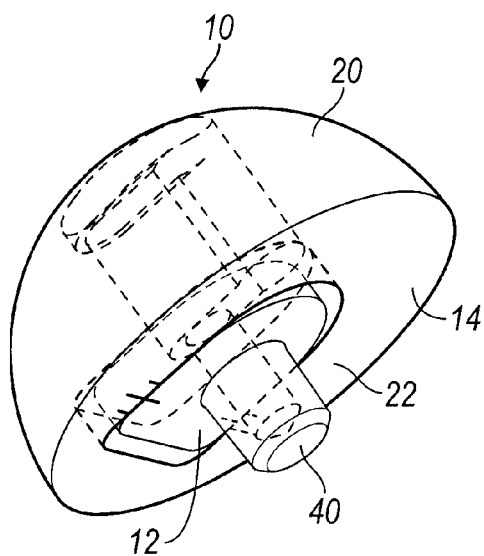
FIG. 2 is a perspective view of the adapter and head components of the device illustrated in FIG. 1 shown in an assembled state.
Figure 3:
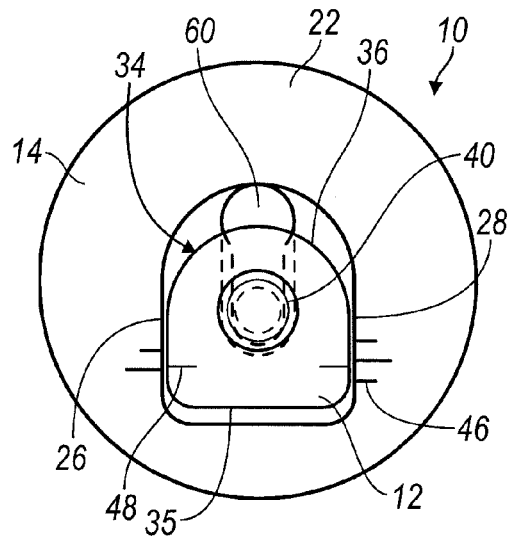
FIG. 3 is a bottom view of the embodiment of the present teachings illustrated in FIG. 1.
Figure 4A:
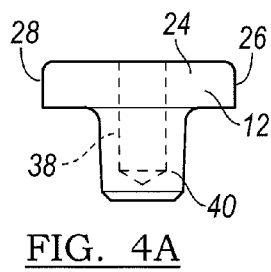
FIGS. 4A-4C are views of the adapter shown in FIG. 1.
Figure 4B:
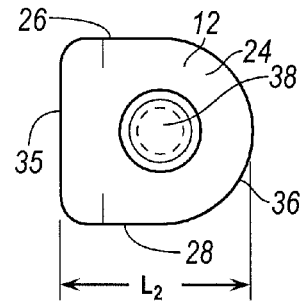
Figure 4C:
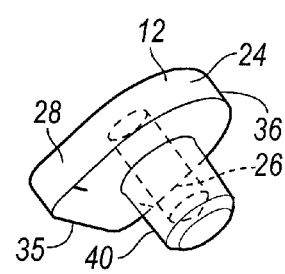
Figure 5A:
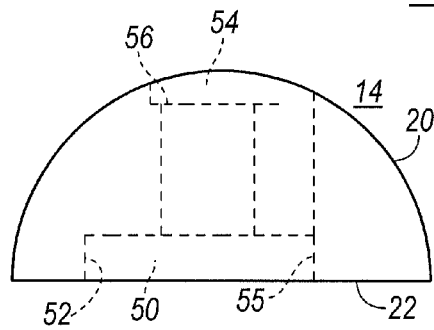
FIGS. 5A-5D are views of the head shown in FIG. 1.
Figure 5C:
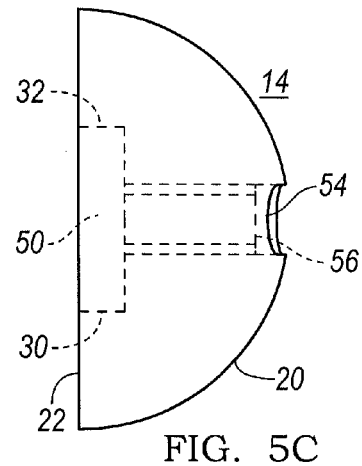
Figure 5B:
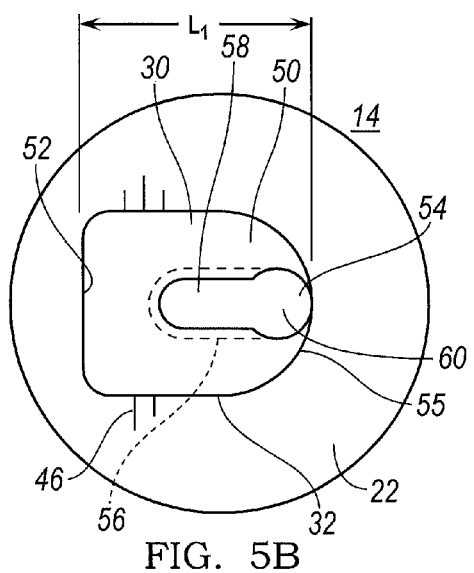
Figure 5D:
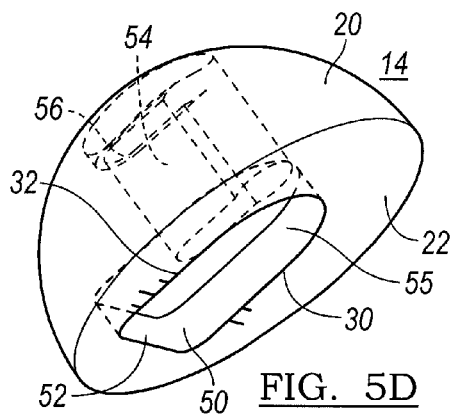

As shown in FIGS. 2 and 3, the bottom surface 34 of the adapter 12 and a bottom surface 22 of the head 14 each have indicia 46 and 48 which indicate the relative positioning of the head 14 with respect to the adapter 12. Additionally, the outer spherical surface 20 has the rotational indicia 43 which is used to determine the relative rotation of the head 14 with respect to the stem 18.

FIGS. 5A-5D represent the head 14 shown in FIG. 1. Defined on the bottom surface 22 is an adapter accepting cavity 50. The cavity 50 has the second pair of bearing surfaces 30 and 32. Additionally, the cavity 50 has flat and curved bearing surfaces 52 and 55 which are configured to interface with the flat and circular bearing surfaces 35 and 36 of the adapter.

The head 14 further defines a through bore 54. The through bore 54 passes through the outer spherical surface 20 and the adapter accepting cavity 50. The through bore 54 has a defined shelf 56 which is configured to support a head portion 57 of the coupling member 16. The through bore 54 further has a slot portion 58 and a circular portion 60 which facilitate transverse movement of the coupling member 16 within the through bore 54. As the cavity 50 has a length $L_1$ which is longer than the length $L_2$ of the adapter 12, the adapter 12 is configured to move transversely within the head 14. The difference in $L_1$ and $L_2$ is the distance of the linear offset of the system. The first pair of bearing surfaces 26 and 28 and second pair of bearing surfaces 30 and 32 are configured so as to prevent relative rotational movement between the adapter 12 and the head 14.

Figure 6:
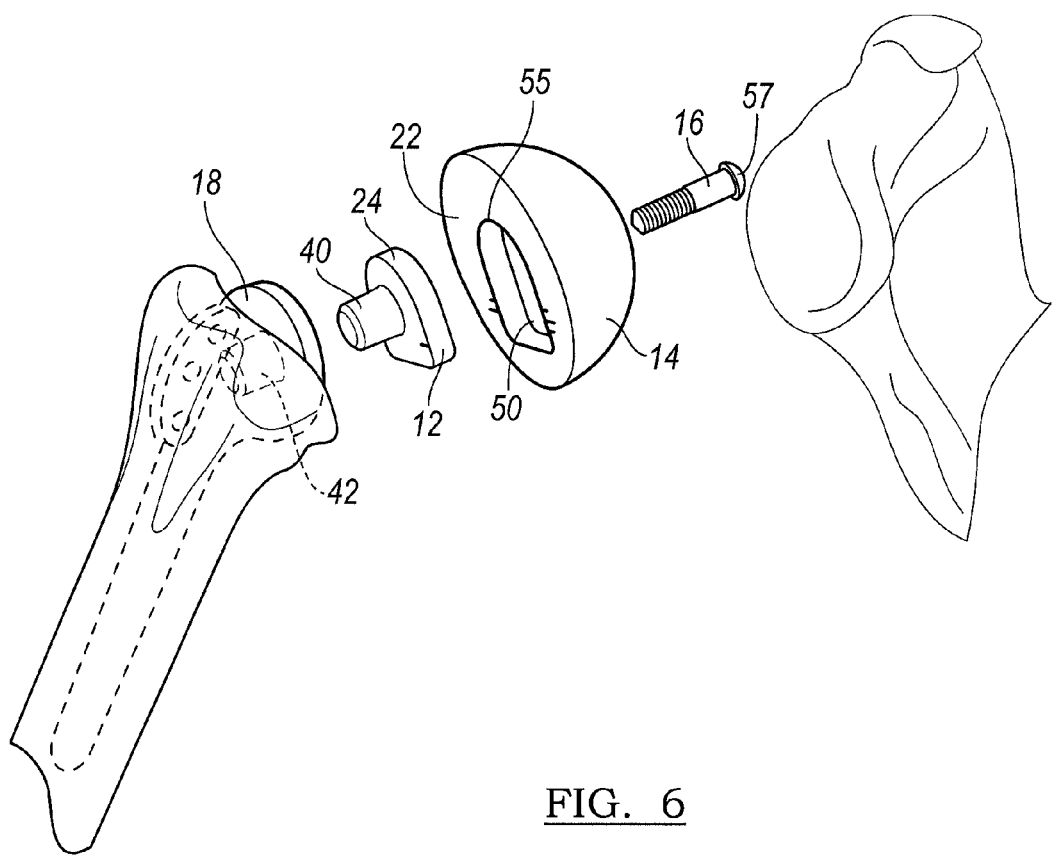
FIG. 6 represents the implantation of the measurement head into a stem component.
Figure 7:
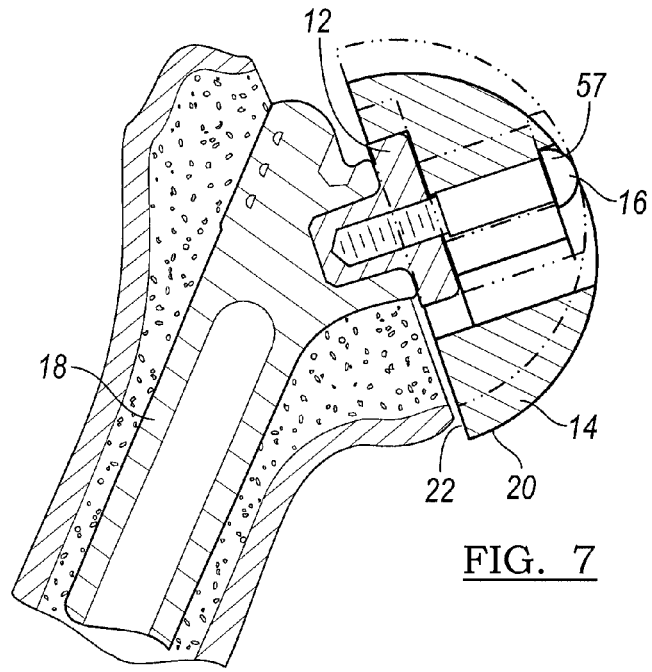
FIG. 7 is cross-sectional view of the trial head coupled to an implanted stem.
Figure 8:
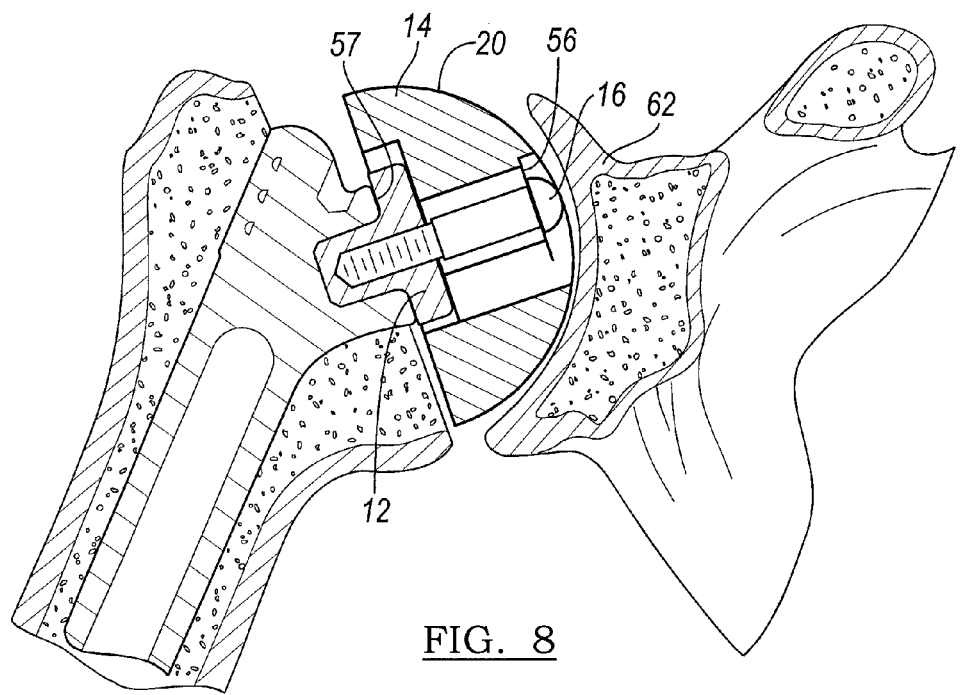
FIG. 8 is cross-sectional view of the trial head coupled to an implanted stem and being positioned into a glenoid.

FIGS. 6-8 show views of the relationship of the measuring device 10 in its environmental surroundings. The tapered coupling portion 40 of the adapter 12 is positioned within the taper 42 of the stem 18. Coupling member 16 passes through the through bore 54 of the head 14 to loosely couple the head 14 to the adapter 12. After, the head 14 is then positioned against a glenoid 62 which can be natural or an implant, and the kinematic action of the head is then tested.

Figure 9:
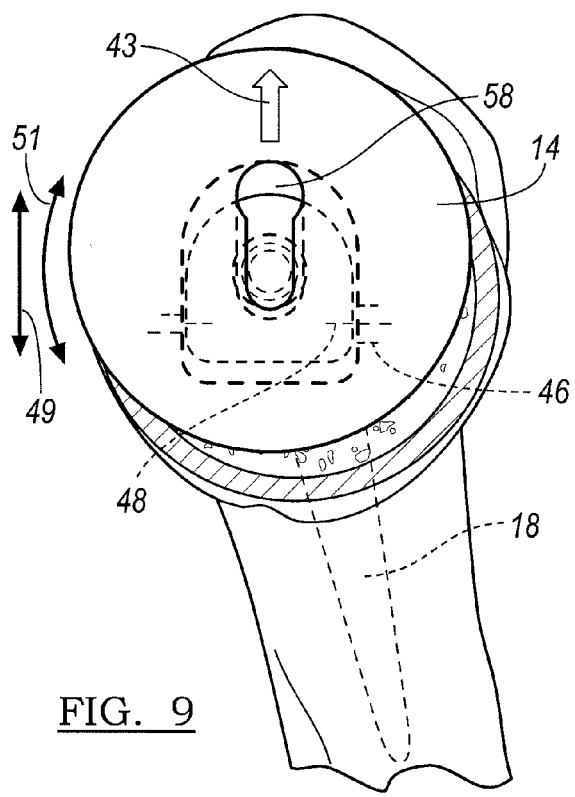
FIGS. 9 and 10 represent the adjustment of the head with respect to the adapter.
Figure 10:
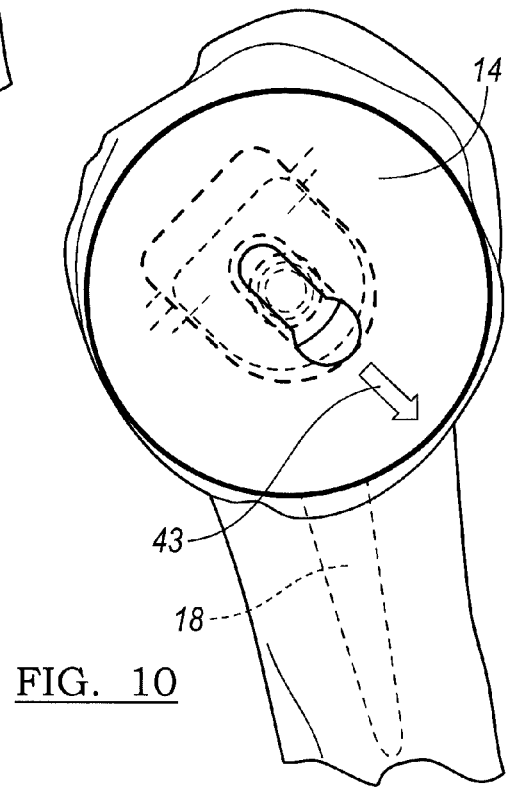
Figure 11:
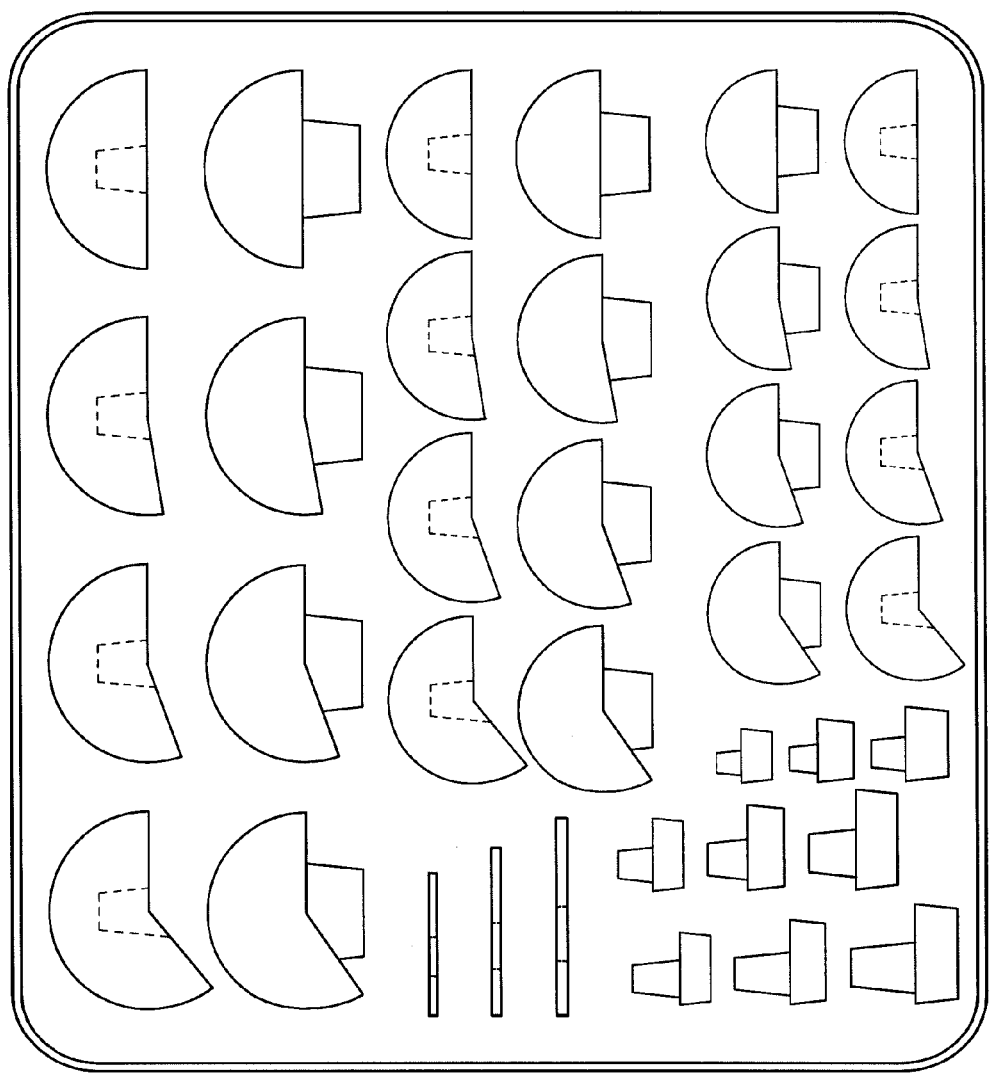
FIG. 11 represents a kit of components.

As seen in FIGS. 8 and 9, should a physician determine that adjustment is necessary, the radial offset 49 of the head 14 can be accomplished by moving it in a first degree of freedom relative to the adapter 12. After this adjustment is made, the physician will then tighten the coupling member 16 to fix the radial position of the head 14 with respect to the adapter 12. The physician can then use the indicia 46 and 48 on the lower stem engaging surface or bottom surface 34 of the adapter 12 and bottom surface 22 of the head 14 to determine the appropriate implant to use.

As seen in FIG. 9, the adapter 12 and head 14 can be rotated 51 in a second degree of freedom with respect to the stem 18. The rotational indicia 43 on the outer spherical surface 20 can be used to mark the relative location of the implant measuring device 10 with respect to the stem 18. This marking can optionally be made on the biologic tissue surrounding the stem 18. This relative rotation marking is then used by the physician to determine the rotational alignment of the offset implant prior to implantation.

The description of the disclosure is merely exemplary in nature and, thus, variations that do not depart from the gist of the disclosure are intended to be within the scope of the disclosure. Such variations are not to be regarded as a departure from the spirit and scope of the disclosure.

What is claimed is:

1. A method of trialing an implant, the method comprising:
   coupling a head portion to an adapter having a coupling axis;
   displacing the head with respect to an articulating surface;

rotating the head about the coupling axis with respect to the articulating surface; and displacing the head with respect to the adapter from a first position to a second position along a straight linear path defined by a pair of flat bearing surfaces of the adapter, generally perpendicular to the coupling axis with respect to the adapter.

2. The method according to claim 1 further comprising rotating the adapter relative to a prosthetic fixation component.

3. The method according to claim 2 further comprising placing an indication of the relative rotation of the head on a biological tissue.

4. The method according to claim 2 further comprising reading an indicia indicative of the linear translation of the head with respect to the adapter.

5. The method according to claim 4 further comprising selecting at least one prosthesis configured to be coupled to the fixation component from a kit of components depending on the reading of the indicia.

6. The method according to claim 1 further comprising fixably coupling the head to the adapter after linearly translating the head with respect to the adapter.

7. A method of trialing an implant, the method comprising:
coupling a head to an adapter having a coupling axis, wherein a portion of the head defines an elongated aperture having first and second ends defining a generally flat interface surface, and the adapter defines a pair of flat bearing surfaces configured to mate with the first and second ends such that the adapter is linearly positionable within the elongated aperture; and displacing the head with respect to the adapter from a first position to a second position along a straight linear path defined by the pair of flat bearing surfaces of the adapter, generally perpendicular to the coupling axis with respect to the adapter.

8. The method according to claim 7 further comprising rotating the adapter relative to a prosthetic fixation component.

9. The method according to claim 8 further comprising reading an indicia indicative of the linear translation of the head with respect to the adapter.

10. The method according to claim 9 further comprising selecting at least one prosthesis configured to be coupled to a fixation component from a kit of components depending on the reading of the indicia.

11. The method according to claim 7 further comprising fixably coupling the head to the adapter after linearly translating the head with respect to the adapter.

* * * * *